(12) United States Patent
Kauphusman et al.

(10) Patent No.: US 9,572,583 B2
(45) Date of Patent: *Feb. 21, 2017

(54) METHODS AND SYSTEMS FOR OCCLUDING VESSELS DURING CARDIAC ABLATION

(75) Inventors: James V. Kauphusman, Champlin, MN (US); Andre d'Avila, Florianopolis-Santa Catatina (BR); Vivek Y. Reddy, New York, NY (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 648 days.

This patent is subject to a terminal disclaimer.

(21) Appl. No.: 12/785,140

(22) Filed: May 21, 2010

(65) Prior Publication Data

US 2010/0292687 A1 Nov. 18, 2010

Related U.S. Application Data

(63) Continuation-in-part of application No. PCT/US2008/084406, filed on Nov. 21, 2008.

(Continued)

(51) Int. Cl.
*A61B 18/12* (2006.01)
*A61B 17/12* (2006.01)
(Continued)

(52) U.S. Cl.
CPC ..... *A61B 17/12036* (2013.01); *A61B 17/1204* (2013.01); *A61B 17/12109* (2013.01);
(Continued)

(58) Field of Classification Search
CPC ... A61B 18/082; A61B 18/14; A61B 18/1492; A61B 18/24; A61B 2018/00577; A61B 2018/00404; A61B 2018/0022; A61B 2018/0212; A61B 2018/00267; A61B 2018/00214; A61B 2018/1816; A61B 2018/00351; A61B 2018/00285; A61B 2018/00345; A61B 2018/00317; A61B 2018/1475; A61B 17/00; A61B 17/320725; A61B 17/12136; A61B 17/12036; A61B 17/12045; A61B 17/12109; A61B 2017/22051; A61B 2017/22067; A61B 5/6853; A61B 5/6858; A61B 5/4836; A61B 5/6852

(Continued)

(56) References Cited

U.S. PATENT DOCUMENTS

| 4,838,268 A | 6/1989 | Keith |
| 5,090,958 A * | 2/1992 | Sahota ..................... 604/98.01 |

(Continued)

OTHER PUBLICATIONS

Fuller, et al. "Intramural Coronary Vasculature Prevents Transmural Radiofrequency Lesion Formation: Implications for Linear Ablation". Circulation: Journal of the American Heart Association, Mar. 24, 2003. 8 pgs.

(Continued)

*Primary Examiner* — Michael Peffley
*Assistant Examiner* — Khadijeh Vahdat
(74) *Attorney, Agent, or Firm* — Dykema Gossett, PLLC.

(57) ABSTRACT

A method is provided for ablating a portion of the myocardium. The method includes inserting an occlusion catheter into a vessel on a heart, occluding the vessel using the occlusion catheter, inserting an ablation catheter into a chamber of the heart, positioning the ablation catheter against the myocardium, and ablating a portion of the myocardium while the vessel is occluded. The system includes an occlusion catheter having a catheter body including a tubular member having a distal portion and a bend located in the distal portion, a balloon located proximal of the bend and configured to contact an inner surface of the (Continued)

coronary sinus when positioned therewithin, a plurality of marker bands positioned on the catheter body, and a plurality of electrodes positioned on the catheter body.

19 Claims, 2 Drawing Sheets

Related U.S. Application Data

(60) Provisional application No. 60/989,807, filed on Nov. 21, 2007, provisional application No. 61/232,260, filed on Aug. 7, 2009.

(51) Int. Cl.
*A61B 18/14* (2006.01)
*A61B 18/00* (2006.01)

(52) U.S. Cl.
CPC .. *A61B 17/12122* (2013.01); *A61B 17/12136* (2013.01); *A61B 18/1492* (2013.01); *A61B 2018/00214* (2013.01); *A61B 2018/00285* (2013.01); *A61B 2018/00577* (2013.01); *A61B 2018/00797* (2013.01); *A61B 2018/00815* (2013.01); *A61B 2018/00821* (2013.01)

(58) Field of Classification Search
USPC ............................................ 606/41; 604/509
See application file for complete search history.

(56) References Cited

U.S. PATENT DOCUMENTS

| | | | | |
|---|---|---|---|---|
| 5,417,689 | A | | 5/1995 | Fine |
| 5,540,679 | A | * | 7/1996 | Fram et al. ..................... 606/27 |
| 5,735,290 | A | * | 4/1998 | Sterman et al. ............... 128/898 |
| 5,738,652 | A | * | 4/1998 | Boyd et al. ................ 604/96.01 |
| 5,775,327 | A | * | 7/1998 | Randolph et al. ............. 600/374 |
| 2001/0007070 | A1 | * | 7/2001 | Stewart et al. .................. 606/41 |
| 2001/0021849 | A1 | | 9/2001 | Swartz |
| 2002/0010419 | A1 | | 1/2002 | Jayaraman |
| 2002/0013548 | A1 | * | 1/2002 | Hinchliffe ................ 604/101.01 |
| 2002/0026182 | A1 | | 2/2002 | Joye |
| 2002/0038120 | A1 | * | 3/2002 | Duhaylongsod et al. ...... 606/15 |
| 2002/0042611 | A1 | * | 4/2002 | Sliwa et al. .................... 606/27 |
| 2002/0087156 | A1 | * | 7/2002 | Maguire et al. ................ 606/41 |
| 2002/0183730 | A1 | | 12/2002 | Reu et al. |
| 2004/0034347 | A1 | * | 2/2004 | Hall et al. ........................ 606/41 |
| 2005/0059883 | A1 | | 3/2005 | Peterson |
| 2005/0065504 | A1 | * | 3/2005 | Melsky et al. .................. 606/16 |
| 2006/0058775 | A1 | * | 3/2006 | Stevens et al. ............... 604/509 |
| 2006/0069385 | A1 | * | 3/2006 | Lafontaine ............ A61B 18/02 606/21 |
| 2006/0276710 | A1 | | 12/2006 | Krishnan |
| 2007/0129720 | A1 | * | 6/2007 | Demarais et al. .............. 606/41 |
| 2008/0249463 | A1 | | 10/2008 | Pappone |

OTHER PUBLICATIONS

Takahashi, et al. "Acute Occlusion of the Left Circumflex Coronary Artery During Mitral Isthmus Linear Ablation", J Cardiovasc Electrophyiol, Vo. 16, pp. 1104-1107, Oct. 2005.

Thyer, et al. "Protection of the Coronary Arteries During Epicardial Radiofrequency Ablation with Intracoronary Chilled Saline Irrigation: Assessment in an In Vitro Model", J Cardiovasc Electrophysiol, vol. 17, pp. 544-549, May 2006.

* cited by examiner

METHODS AND SYSTEMS FOR OCCLUDING VESSELS DURING CARDIAC ABLATION

CROSS-REFERENCE TO RELATED APPLICATIONS

This application is a continuation-in-part of international patent application no. PCT/US2008/084406 filed 21 Nov. 2008 (the '406 application) which in turn claims the benefit of U.S. provisional application No. 60/989,807 filed 21 Nov. 2007, (the '807 application), and the instant application furthermore claims the benefit of U.S. provisional patent application No. 61/232,260 filed 7 Aug. 2009 (the '260 application). The '406, the '807, and the '260 applications are hereby incorporated by reference as though fully set forth herein. The instant application is also related to non-provisional U.S. patent application Ser. No. 12/785,227 filed 21 May 2010, the contents of which are also fully incorporated herein.

BACKGROUND OF THE INVENTION a. Field of the Invention

The field of the invention relates generally to cardiac ablation, and, more particularly, to vascular occlusion during cardiac ablation.

b. Description of Related Art

Atrial fibrillation is a form of arrhythmia and results from disorganized electrical activity in the heart muscle, or myocardium. As a result of abnormalities in the heart's electrical activity, the heart does not beat effectively and it is not able to pump the blood out properly.

Ablation of the mitral isthmus, defined as a narrow region between the mitral annulus and the left inferior pulmonary vein ostium, appears to increase the success rate of treating chronic atrial fibrillation. However, it is difficult to create transmural lesions in this region, even though the myocardial thickness in the mitral isthmus is not particularly greater than in other regions of the left atrium. Incomplete or non-continuous lesions and/or unidirectional mitral isthmus block can be problematic as it may result in recurrence of arrhythmia and/or a proarrhythmic effect by slowing conduction through the mitral isthmus. High-power endocardial ablations, as well as delivery of radio frequency (RF) energy into the coronary sinus and the great cardiac vein (epicardial portion of the mitral isthmus), are frequently used to prevent incomplete lines. This combined epicardial/endocardial approach allows for bidirectional isthmus block to be achieved.

BRIEF DESCRIPTION OF THE INVENTION

In one aspect, a method is provided for ablating a portion of the myocardium. The method includes inserting an occlusion catheter into a vessel on a heart, occluding the vessel using the occlusion catheter, inserting an ablation catheter into a chamber of the heart, positioning the ablation catheter against the myocardium, and ablating a portion of the myocardium while the vessel is occluded.

In another aspect, a method is provided for ablating a portion of the atrial myocardium. The method includes inserting a balloon catheter into a coronary sinus, inserting an ablation catheter into a left atrium of a heart, and ablating a portion of the atrial myocardium while a balloon on the balloon catheter is expanded.

In a further aspect, an occlusion catheter is provided that includes a catheter body including a tubular member having a distal portion and a bend located in the distal portion. The occlusion catheter also includes a balloon located proximal of the bend and configured to contact an inner surface of the coronary sinus when positioned therewithin. A plurality of marker bands are positioned on the catheter body and a plurality of electrodes also are positioned on the catheter body. In one embodiment, the proximal end of the catheter shaft comprises a braided catheter shaft constructed for example with 304 stainless steel braid incorporated into a nylon 11 polymer. An exemplary dimension for the braid is about 0.002" by about 0.006" (individual filars). Of course, other suitable types, or grades, of stainless steel can be utilized when practicing the teaching herein, including a braid having one or more substantially flat cross-sectional dimensions (e.g., a "flat braid"). In one form of the invention the braid, or flat braided portions, are disposed at least adjacent the proximal portion of the balloon. That is, the occlusion catheter shaft may also include a braided catheter portion wherein the catheter wall includes a cylindrical and/or flat braid of metal fibers, for example, stainless steel fibers (for from about a foot or so proximal to the balloon to the entire length of the catheter shaft). Such a metallic braid may be included in the catheter to add stability to the catheter and also to resist radial forces that might crush the catheter. Metallic braid also provides a framework to translate force imparted by the clinician on the proximal end of the catheter to the distal end to urge an occlusion structure, such as a balloon, disposed on the catheter into a desired, or appropriate, location, for example. The flat wire, or other types of wire, braid can be thought of as a so-called backbone for the catheter. In this regard non-provisional U.S. patent application Ser. No. 11/723,729 filed 21 Mar. 2007 assigned to St. Jude Medical, Atrial Fibrillation Division, Inc. (now U.S. Pat. No. 7,706,891) is hereby incorporated herein in its entirety. Other materials can be used to fabricate the backbone portion provided that they have appropriate mechanical characteristics. One reason for including the braided catheter shaft is that stiffer shaft material is desirable, if not simply necessary, to help the catheter maintain its position within the CS when the balloon is inflated and thus continue to occlude the CS. This characteristic of a catheter is sometimes referred to as having adequate "pushability" in certain contexts. The occlusion catheter can also include a deflection, or steering, mechanism for the distal portion to aid placement at or near the CS. In lieu of or in addition to such a catheter steering mechanism (e.g., one, two or more pull wires anchored to a ring in the distal portion) a separate steerable introducer can be utilized to deploy the occlusion catheter. An Agilis™ brand introducer from St. Jude Medical, Inc. could be used and a steerable handle system, such as that taught in U.S. Pat. No. 7,691,095 entitled, "Bi-directional steerable catheter control handle," to Bednarek et al. would also provide insight into such a system or kit. The '095 patent is hereby incorporated herein in its entirety as if fully set forth herein.

In a further aspect, a method is provided for creating a bi-directional mitral isthmus block in a heart. The method includes inserting an occlusion catheter into a coronary sinus of the heart, inserting an ablation catheter into a left atrium of the heart, expanding a balloon on the occlusion catheter, and ablating a portion of the myocardium to create a bi-directional isthmus block while the balloon is expanded.

DETAILED DESCRIPTION OF THE INVENTION

The invention set forth below in detail is a method and system to create ablation lines in the myocardium. Prior to initiation of the ablation, an occlusion catheter is positioned within a vessel, such as the coronary sinus, to completely or substantially prevent blood flow therethrough during the ablation procedure. Endocardial ablation is then initiated while the coronary sinus is occluded. It has been found that ablation lines, or lesions, extending completely through the myocardium (i.e., transmural lesions) that are created near the coronary sinus after it has been occluded are formed more easily than if the coronary sinus were not occluded. In the example set forth below, it is shown that occlusion of the coronary sinus during the creation of a mitral isthmus ablation line occurs with less power than would be used without occlusion of the coronary sinus and/or the time for creation of the ablation line is shorter.

The system and methods set forth below are not limited to the specific embodiments described herein. In addition, components of each system and steps of each method can be practiced independently and separately from other components and method steps described herein. Each component and method step also can be used in combination with other catheters, balloons, systems, and methods.

Figure 1:
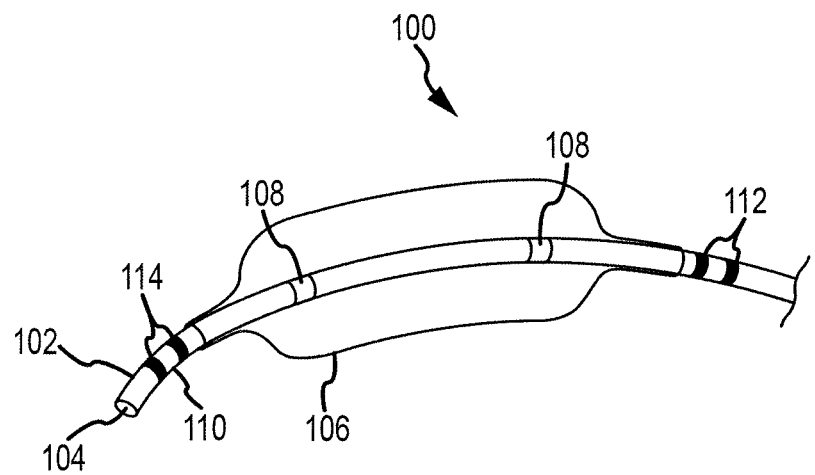
FIG. 1 is a schematic view of a coronary sinus occlusion system in accordance with one embodiment of the invention.

FIG. 1 illustrates a coronary sinus occlusion system 100 in accordance with one embodiment of the invention. System 100 includes a catheter 102 having a distal end 104 and a proximal end (not shown). Catheter 102 has a tubular body with a passageway extending therethrough. A balloon 106 is located near distal end 104. In one embodiment, balloon 106 is a polyurethane balloon located 1.5 cm from distal end 104. It should be recognized that balloon 106 could be manufactured from other materials and could be located closer or further from distal end 104 than 1.5 cm. In another embodiment, balloon 106 is manufactured from an elastomeric material such as silicone. As shown in FIG. 1, balloon 106 has a substantially cylindrical shape.

Catheter 102 also includes a plurality of spaced apart marker bands 108 located under balloon 106. In one embodiment, catheter 102 includes two marker bands 108 manufactured from a radio-opaque material, as known in the art, to allow for fluoroscopic visualization of catheter 102. In another embodiment, marker bands 108 are located on catheter 102 at locations other than under balloon 106.

Catheter 102 includes a bend 110 located between balloon 106 and distal end 104. Bend 110 facilitates cannulization of the coronary sinus by allowing easier access to the coronary sinus opening. In one embodiment, bend 110 is between 25 and 75 degrees, and more particularly between 30 and 60 degrees, and more particularly still, is about 45 degrees. In one embodiment, bend 110 is located within 4 centimeters of distal end 104, and more particularly is located within 2 centimeters of distal end 104, and more particularly still, is located about 1.5 centimeters from distal end 104. In addition, catheter 102 is curved proximally of bend 110. This curvature further facilitates cannulization of the coronary sinus as well as proper placement of balloon 106 within the coronary sinus.

Catheter 102 also includes a pair of electrodes 112, 114. A first electrode 112 is located on catheter 102 proximally of balloon 106 and a second electrode 114 is located on catheter 102 distally of balloon 106. Electrodes 112 and 114 are utilized to detect the presence and absence of errant electrical signals in the myocardium (wall of the heart). Each electrode 112, 114, is connected to a lead (not shown) that extends along catheter 102. In one embodiment, each electrode is a ring electrode.

Figure 2:
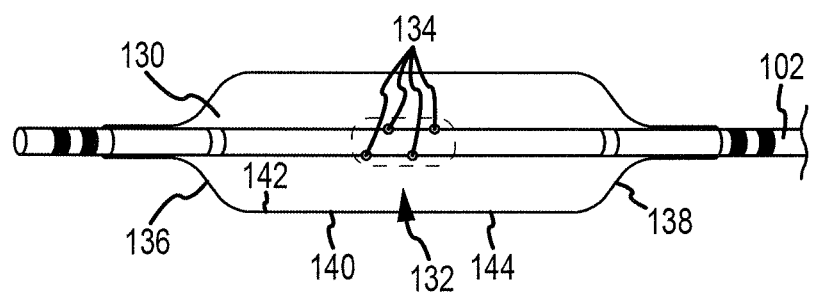
FIG. 2 is a schematic view of an alternative balloon to be used with the catheter shown in FIG. 1.

FIG. 2 illustrates an alternative balloon 130 suitable for use with catheter 102. Balloon 130 is similar to balloon 106 except that balloon 130 includes a temperature sensing array 132 having multiple sensors 134 positioned such that accurate temperature readings can be obtained of adjacent tissue. Sensors 134 are positioned at a first end 136 and/or a second end 138 of balloon 130, at a middle 140 of balloon 130, or at any location along balloon 130. In one embodiment, sensors 134 are miniature T-type thermocouples, thermistors, or any other type of sensor that can be utilized to sense temperature of adjacent tissue. In exemplary embodiments, sensors 134 are disposed against an interior surface 142 of balloon 130, an exterior surface 144 of balloon 130 and/or within balloon 130 and spaced apart from interior surface 142 of balloon 130.

As shown in FIG. 1, catheter 102 is curved and, accordingly, includes an inner curvature. Array 132 is located at the inner curvature to facilitate positioning of thermocouple array 132 in the area of the mitral isthmus ablation line. In one embodiment, a marker is positioned proximate array 132 to facilitate accurate orientation of balloon 130 with regard to the atrial portion of the coronary sinus. As shown in FIG. 2, four sensors 134 are arranged in an array that is 2 mm wide by 6 mm long, with 2 mm spacing between sensors. Leads (not shown) extend from each sensor 134 along catheter 102 to a multiple channel data logger (not shown) connected to a standard computer (not shown) via an RS 232 serial link (not shown).

Figure 3:
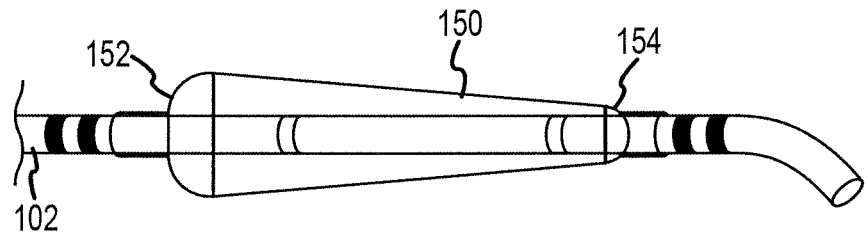
FIG. 3 is a schematic view of a further alternative balloon to be used with the catheter shown in FIG. 1.

FIG. 3 illustrates a further alternative balloon 150 suitable for use with catheter 102. Balloon 150 has a rounded frusto-conical shape that tapers from a proximal end 152 to a distal end 154. In one embodiment, the taper is about a 7 degree included angle.

Catheter 102 includes an inflation port (not shown) that is used to supply fluid to balloons 106, 130 and 150. In one embodiment, the inflation fluid is a gas such as air or $CO_2$. In another embodiment, the inflation fluid is a liquid such as saline or water.

Figure 4:
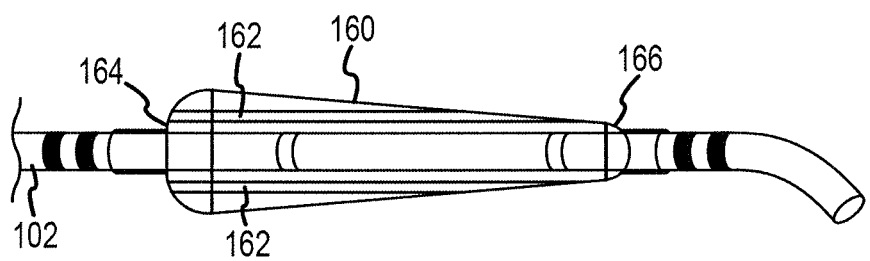
FIG. 4 is a schematic view of a further alternative balloon to be used with the catheter shown in FIG. 1.

FIG. 4 illustrates an alternative balloon 160 positioned on catheter 102. Balloon 160 includes a plurality of passageways 162 extending from a proximal end 164 of balloon 160 to a distal end 166 of balloon 160. Passageways 162 permit blood to flow therethrough while balloon 160 is inflated and contacting an interior surface of the vessel into which catheter 102 has been positioned. Passageways 162 are configured such that blood flow will be spaced from the vessel wall thus permitting a fluid gap to be located between the flowing blood and the vessel wall. The fluid filling balloon 160 is, in one embodiment, a gas such as one of air and $CO_2$. Alternatively, the fluid is a liquid such as water or saline.

Figure 5:
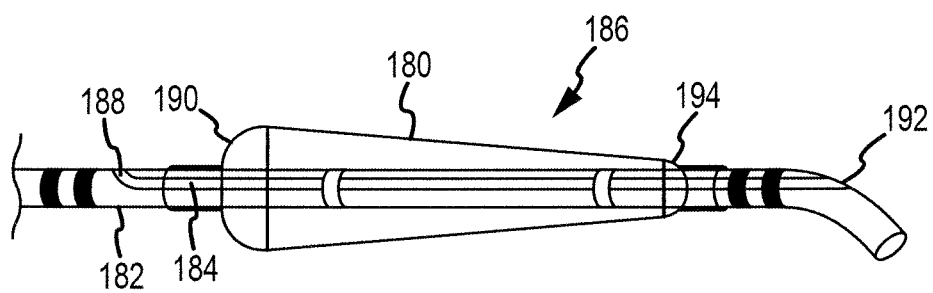
FIG. 5 is a schematic view of a further alternative balloon to be used with an alternative catheter.

FIG. 5 illustrates a further alternative balloon 180 positioned on catheter 182. A passageway 184 extends through a distal portion 186 of catheter 182. Passageway 184 includes a first opening 188 at a position proximal of a proximal end 190 of balloon 180 and a second opening 192 at a position distal of a distal end 194 of balloon 180. In operation, blood is permitted to flow through passageway 184 when balloon 180 is expanded and contacting an interior surface of the vessel into which catheter 182 has been positioned.

The method of using the above described coronary sinus occlusion system (shown in FIGS. 1-3) will next be described.

A sheath containing the occlusion catheter is inserted into one of the femoral artery and the internal jugular. In one embodiment, the sheath is an 8Fr, Fast Cath®, available from St. Jude Medical, Minnetonka, Minn. The sheath is manipulated through the vascular system so that it enters a chamber of the heart, such as the left atrium. The occlusion catheter is extended distally from the sheath until the balloon on the catheter is distal of the distal end of the introducer sheath. The catheter is manipulated to allow a distal tip of the catheter to enter the vessel to be occluded. The extended catheter is inserted into the vessel such that the balloon is at least partially within the vessel. In one embodiment, the vessel is the coronary sinus and the balloon is completely contained within the vessel and located adjacent to, and/or overlying, a portion of the myocardium to be ablated. In the embodiment illustrated in FIGS. 1-3, a pair of marker bands is included on the catheter. These marker bands allow accurate placement of the catheter within the vessel to be occluded.

An ablation catheter is then manipulated through the vascular system so that the ablation catheter enters a chamber of the heart, such as the left atrium. In one embodiment, the ablation catheter also includes diagnostic capability used to map relevant geometries and/or electrical activity within the chamber. When the ablation catheter is located within the left atrium, such geometries include one or more of the left atrial appendage, the right superior pulmonary vein, the inferior pulmonary trunk, and the left atrial body. In an alternative embodiment, the above described mapping is performed using a separate mapping system coupled to a mapping and/or therapy delivery catheter. An exemplary mapping system includes the EnSite NavX, available from St. Jude Medical, St. Paul Minn.

The ablation catheter is then utilized to ablate portions of the myocardium. The ablation energy and delivery technology includes, by way of example and without limitation one or more of the following: cryogenic, radiofrequency (RF), laser, ultrasound (including high intensity focused ultrasound, or HIFU) and microwave. In one embodiment, ablation lesions are created on the atrial myocardium overlying the coronary sinus. The ablation lesions extend through the myocardium and prevent errant electrical signals from passing across the portion of the myocardium that has been ablated. In an exemplary embodiment, an ablation lesion is created that extends from proximate the left inferior pulmonary vein to proximate the mitral valve. Such an ablation lesion is sometimes referred to as a mitral isthmus line. It is this region of the myocardium that overlies the coronary sinus. Accordingly, when the coronary sinus is occluded, blood does not flow adjacent this portion of the myocardium and it has been found that a lower power setting can be used on the ablation catheter and/or the ablation is completed within a shorter time, than when blood is flowing through the coronary sinus.

According to an aspect of the invention a gas filled balloon is located within the portion of the coronary sinus that is adjacent to, and/or overlies this portion of the myocardium, and thus heat is not removed from the myocardium as efficiently as when blood is flowing through the coronary sinus. The absence of blood flow thus allows more efficient and relatively rapid ablation of this portion of the myocardium. In one embodiment, due at least in part to this increased efficiency, ablating within the coronary sinus is not used when the above described coronary sinus occlusion catheter is used. In another embodiment, due at least in part to the increased efficiency, the number of ablation lesions created when the above described coronary sinus occlusion catheter is used is less than when the coronary sinus occlusion catheter is not used.

In order to reliably engage the CS a segment or region of reinforcement in an exemplary embodiment a portion of the catheter shaft is fabricated to enhance the so-called pushability of the distal end and, in particular to promote stability of the balloon in the CS during CS occlusion. The structural reinforcement can include an embedded braided segment of the shaft of the catheter including one or more flat wire filars (e.g., wire having a lateral dimension greater than an axial dimension). The structural reinforcement can extend partially or wholly toward the proximal end of the catheter but in the case that the catheter is deployed within a delivery sheath or introducer, the structural reinforcement does not necessarily need to extend all the way to the proximal end of the catheter.

As described above, located on the occlusion catheter is a pair of electrodes. These electrodes are utilized to determine whether errant electrical signals are passing through the portion of the myocardium being monitored. In one embodiment, the occlusion catheter is used to monitor these signals before, during, and/or after the ablation procedure, and to gather information so that a determination can be made as to whether the ablation procedure has stopped the errant electrical signals.

In a further embodiment, the occlusion system includes an introducer sheath utilized to position the occlusion catheter at the coronary sinus. In this embodiment, the catheter extends through the introducer sheath and, upon arrival at the coronary sinus, is extended distally beyond a distal end of the introducer sheath. In one embodiment, the sheath is a steerable sheath that can be manipulated through the use of wires or other means to bend or curve as it passes through the vascular system, thus bending or curving the catheter therewithin.

EXAMPLE A

Experiments were conducted on nine female pigs using the above identified occlusion system. Vascular access was obtained via standard angiography sheaths in the right femoral artery (8Fr, Fast Cath®, available from St. Jude Medical, Minnetonka, Minn.) and the right internal jugular (10Fr).

Transseptal access was obtained under fluoroscopic guidance with a Daig SL-1 sheath (available from St. Jude Medical, St. Paul, Minn.). A quadripolar electrode, placed in the right coronary cusp, was used as a reference for the electroanatomical mapping system (EnSite NavX, St. Jude Medical, St. Paul, Minn.). Separate geometries and associated electrical activity of the left atrial appendage, the right superior pulmonary vein, the inferior pulmonary trunk, and the left atrial body were acquired using a circular mapping catheter.

Ablation was performed using a 3.5 mm Celsius Thermo-Cool (available from Biosense, Diamond Bar, Calif.). A maximum of 35 watts power was used in the last 7 swine and 50 watts were used in the first 2 animals. All RF ablations were performed for 1 minute with an irrigation rate of 30 cc/min.

For each swine, two linear ablations lines (proximal and distal) were created over the atrial myocardium overlying the coronary sinus. The proximal line was placed more between the inferior border of the inferior pulmonary vein trunk and the mitral annulus. The distal line was located between the inferior border of the left atrial appendage and the mitral annulus. In each swine, the coronary sinus was completely occluded with the coronary sinus occlusion balloon during RF ablation for one of the lines. The coronary sinus occlusion balloon was positioned with the center of the balloon under the ablation line. The coronary sinus balloon was then inflated with approximately 5 mls of air and occlusion of the coronary sinus and the great cardiac vein was confirmed by contrast injection through the catheter internal lumen. The position of the line that was created during coronary sinus occlusion was alternated between swine. The coronary sinus balloon was removed during RF application for the ablation line without occlusion to prevent blood flow limitation. Biophysical parameters of each RF application were continuously recorded in the electrophysiology recording system.

The coronary sinus occlusion catheter utilized is illustrated in FIG. 2.

At the end of the procedure, 2,3,5-triphenyl-2H-tetrazolium chloride was administered intravenously and the animals were euthanized with an intravenous injection of Euthasol 20 ml (390 mg pentobarbital sodium and 50 mg phenyloin sodium per ml, Delmarva Laboratory, Midlothian, Va.). A lateral thoracotomy was then performed with an incision through the left 4th intercostal space. The heart was examined in situ for the presence of pericardial bleeding. The endocardial surface of the excised heart was then examined by creating an incision in the left atrium to allow inspection and photography of the left atrial aspect of the mitral isthmus.

The coronary sinus was opened posteriorly through its free wall for inspection of possible dissection and to assess transmurality of each line. Ablation lines were also examined and photographed longitudinally with a macro camera (Nikon D50, Micro Nikkor 60 mm f2.8, Nikon Corporation, Melville, N.Y., USA) to assess transmurality and for off-line measurements. Ablation lesion characteristics were measured using custom software written with the Matlab programming language (Mathworks).

A total of 18 endocardial ablation lines were placed over the coronary sinus for the nine swine used in the study (i.e. a proximal and distal line for each swine). In one swine, the occlusion balloon could not be properly positioned and therefore two lines were placed without coronary sinus occlusion. Therefore, eight ablation lines were placed during coronary sinus balloon occlusion and 10 lines were placed without coronary sinus occlusion. All lines were identified at necropsy. However, at post mortem examination, one of the proximal ablation lines was found to be located within the left atrial appendage superior to the coronary sinus and therefore, this line was not included in the data analysis.

The left atrial wall thickness was 2.9±1.3 mm for the endocardial lines without coronary sinus occlusion and 3.4±1.1 mm for the endocardial lines with coronary sinus occlusion (p=0.5). Similarly, the mean number of RF applications was 6.2±1.5 and 6.3±1.2 respectively during coronary sinus occlusion and when the coronary sinus balloon was not inflated. Catheter temperature and mean power were not significantly different when coronary sinus occlusion was compared to no-occlusion. Moreover, impedance drop was not different between these two conditions.

All linear lesions deployed during coronary sinus occlusion were transmural. Conversely, only 1 out of 10 lines was transmural when the coronary sinus was open. Overall, RF applications were sufficient to create lesion depth up to 76%±18% of the left atrial wall.

No device related adverse events were seen during the procedures. An epicardial hemorrhagic pericarditis was seen in the first animal (compatible with previous myocarditis, and unlikely to be related to the device). These finding were not seen in the subsequent 8 animals. The lungs were normal and the coronary sinus was normal upon post mortem examination in all animals. No blood clots were observed. The balloon was intact in all devices tested.

Example B (below) is intended as illustrative and not limiting as to a procedure performed according to the foregoing.

B. A method for creating a bi-directional mitral isthmus block in a heart, said method comprising:
  inserting an occlusion catheter into a coronary sinus of the heart;
  inserting an ablation catheter into a left atrium of the heart;
  expanding a balloon on the occlusion catheter; and
  ablating, while the balloon is expanded, a portion of the myocardium to create a bi-directional isthmus block.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural or method elements that do not differ from the literal language of the claims, or if they include equivalent structural or method elements with insubstantial differences from the literal languages of the claims.

What is claimed is:

1. A method for ablating a portion of an atrium of a heart using radiofrequency (RF) energy to create resistive heating in the portion, said method comprising:
  inserting an occlusion catheter into a vessel on or in the heart;
  occluding a section of the vessel using the occlusion catheter, wherein the occluded vessel section and the portion of the atrium share and are separated by an intervening myocardial wall;
  inserting an RF ablation catheter into the atrium;
  positioning the RF ablation catheter against an inner surface of the intervening myocardial wall; and
  creating resistive heat in the portion of the atrium to ablate the portion of the atrium while the vessel section is occluded.

2. The method of claim 1 wherein inserting the occlusion catheter comprises inserting the occlusion catheter into a coronary sinus.

3. The method of claim 1 wherein occluding the portion of the vessel comprises inflating a balloon on the occlusion catheter to occlude the portion of the vessel.

4. The method of claim 1 wherein ablating the portion of the atrium comprises one of: creating a mitral isthmus ablation line, creating an endocardial ablation, and creating a transmural lesion in a region between the mitral annulus and the left inferior pulmonary vein ostium.

5. The method of claim 1 further comprising utilizing the occlusion catheter to sense temperatures of adjacent tissues.

6. The method of claim 1 further comprising utilizing an electrode coupled with the occlusion catheter to determine whether errant electrical signals are present in the atrium.

7. A method for ablating a portion of an atrial myocardium using resistive heating of the portion, said method comprising:
- inserting a balloon catheter into a coronary sinus;
- inserting an RF ablation catheter into a left atrium of a heart; and
- creating resistive heat in the portion of the atrial myocardium to ablate the portion of the atrium while a balloon on the balloon catheter is expanded;
- wherein the balloon catheter is expanded in a portion of the coronary sinus that shares an intervening wall with, and is separated by the intervening wall from, the portion of the atrial myocardium.

8. The method of claim 7 further comprising supplying a fluid to the balloon on the balloon catheter and expanding the balloon to contact an inner wall of the coronary sinus.

9. The method of claim 8 wherein expanding the balloon comprises occluding the coronary sinus.

10. The method of claim 7 wherein ablating the portion of the atrial myocardium further comprises ablating the myocardium from proximate the pulmonary vein to proximate the mitral valve.

11. The method of claim 7 further comprising utilizing an electrode coupled with the balloon catheter to determine whether errant electrical signals are present in the myocardium.

12. The method of claim 7 further comprising sensing temperatures of tissues adjacent the balloon during the ablation.

13. An occlusion catheter comprising:
- a catheter body having a distal portion and a pre-formed bend located in the distal portion, the pre-formed bend configured to facilitate cannulization of said distal portion in a coronary sinus;
- a balloon located proximal of the pre-formed bend and comprising an outer wall configured to contact an inner surface of the coronary sinus when inflated and positioned therewithin, wherein the balloon defines:
  - a longitudinal lumen through which said catheter body extends; and
  - at least one passageway extending from a first opening in the outer wall of the balloon to a second opening in the outer wall of the balloon, the at least one passageway having a longitudinal axis centered in the at least one passageway different from an axis centered in the longitudinal lumen, the at least one passageway configured to permit blood to flow through the balloon while the balloon is inflated and contacting the inner surface of the coronary sinus and both the first opening and the second opening are within the coronary sinus;
- a plurality of marker bands positioned on the catheter body; and
- a plurality of electrodes positioned on the catheter body.

14. The occlusion catheter of claim 13 wherein the plurality of marker bands are located within the balloon.

15. The occlusion catheter of claim 13 further comprising at least one sensor attached to one of: an interior surface of the balloon, an exterior surface of the balloon, and within the balloon and spaced apart from an interior surface of the balloon.

16. The occlusion catheter of claim 15 wherein the at least one sensor comprises a temperature sensor configured to detect a temperature of adjacent tissue.

17. The occlusion catheter of claim 13 wherein the occlusion catheter has at least one of: an angle of the pre-formed bend is between 30 and 60 degrees; and the pre-formed bend is located within about two centimeters of a distal end of the catheter body.

18. The occlusion catheter of claim 13 wherein the balloon has one of a tapered shape and a rounded frusto-conical shape.

19. The occlusion catheter of claim 13, wherein the at least one passageway is parallel with the longitudinal lumen.

* * * * *